Figure 1:
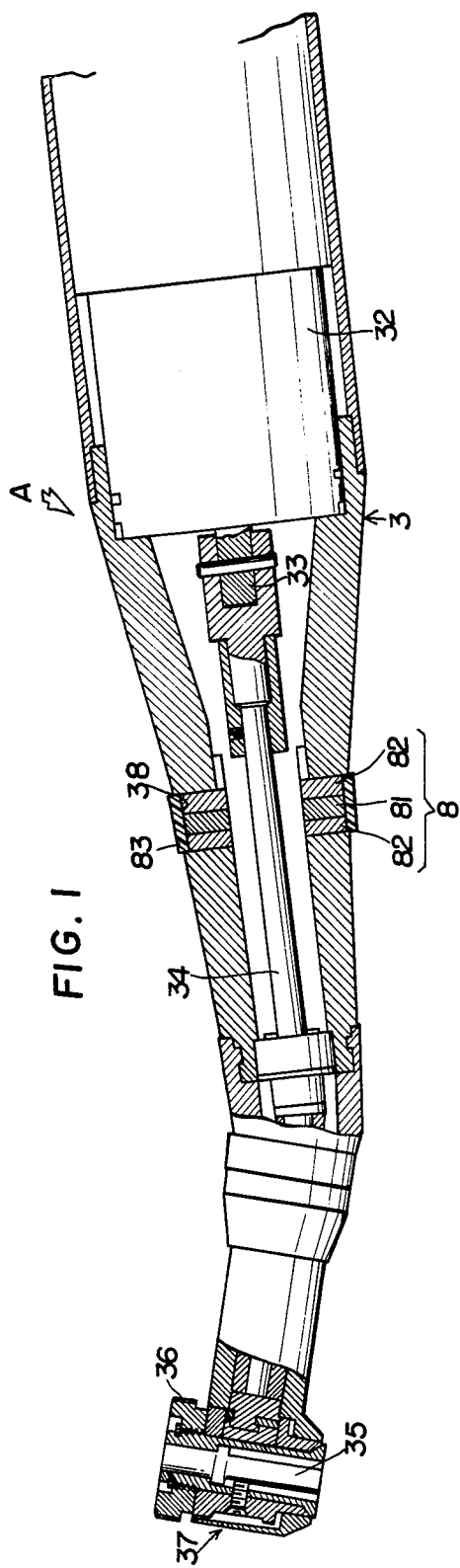

United States Patent [19]
Arai

[11] 4,243,388
[45] Jan. 6, 1981

[54] DENTAL HAND ENGINE

[75] Inventor: Toshio Arai, Tokyo, Japan

[73] Assignee: Kabushiki-Kaisha Dentronics, Tokyo, Japan

[21] Appl. No.: 32,241

[22] Filed: Apr. 20, 1979

[30] Foreign Application Priority Data

Apr. 20, 1978 [JP] Japan ................................. 53-52345

[51] Int. Cl.³ .............................................. A61C 1/00
[52] U.S. Cl. ...................................... 433/27; 433/75; 433/99; 433/102; 433/224
[58] Field of Search ........................ 433/27, 28, 72, 75, 433/98, 99, 102, 224

[56] References Cited
U.S. PATENT DOCUMENTS

| 1,366,877 | 1/1921 | Craig | 433/102 |
| 1,713,971 | 5/1929 | Lowry et al. | 433/224 |
| 3,346,958 | 10/1967 | Sinatra et al. | 433/99 |
| 3,660,901 | 5/1972 | Inoue | 433/102 |
| 3,839,797 | 10/1974 | Randolph | 433/27 |
| 3,916,529 | 11/1975 | Mousseau | 433/224 |

Primary Examiner—Gene Mancene
Assistant Examiner—John J. Wilson
Attorney, Agent, or Firm—Shlesinger, Fitzsimmons & Shlesinger

[57] ABSTRACT

A dental hand engine for driving a reamer for widening root canals, which is characterized in the provision of a control device which electrically senses the time when a forward end of the reamer reaches a radical apex for automatically stopping the engine and consequently the reamer.

1 Claim, 5 Drawing Figures

DENTAL HAND ENGINE

This invention relates to a dental instrument, and more particularly, it relates to a dental hand engine for driving a reamer for widening root canals of teeth, which is characterized in that it is provided with a control device which electrically senses the time when a forward end of the reamer reaches a radical apex, whereby it stops the engine.

This invention shall be explained hereinafter more in detail and more clearly, in conjunction with the accompanying drawings in which a preferred embodiment of this invention is illustrated.

Figure 2:
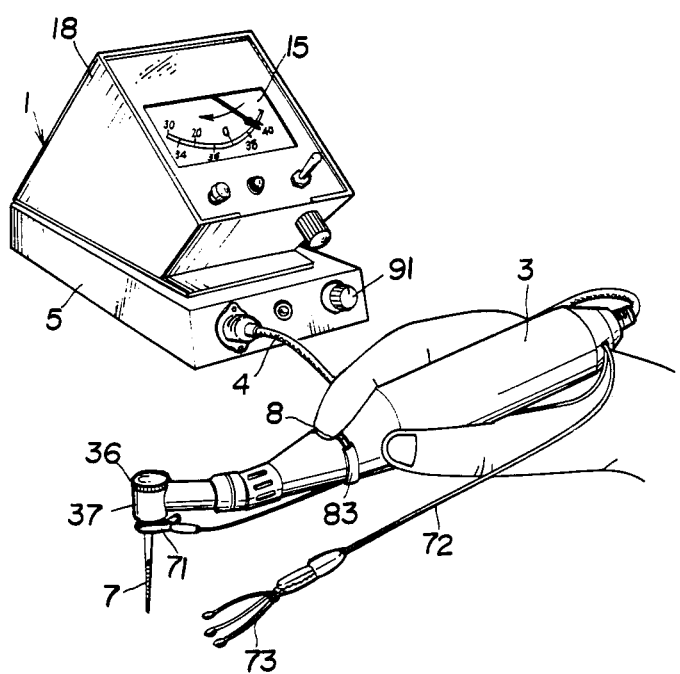
Figure 3:
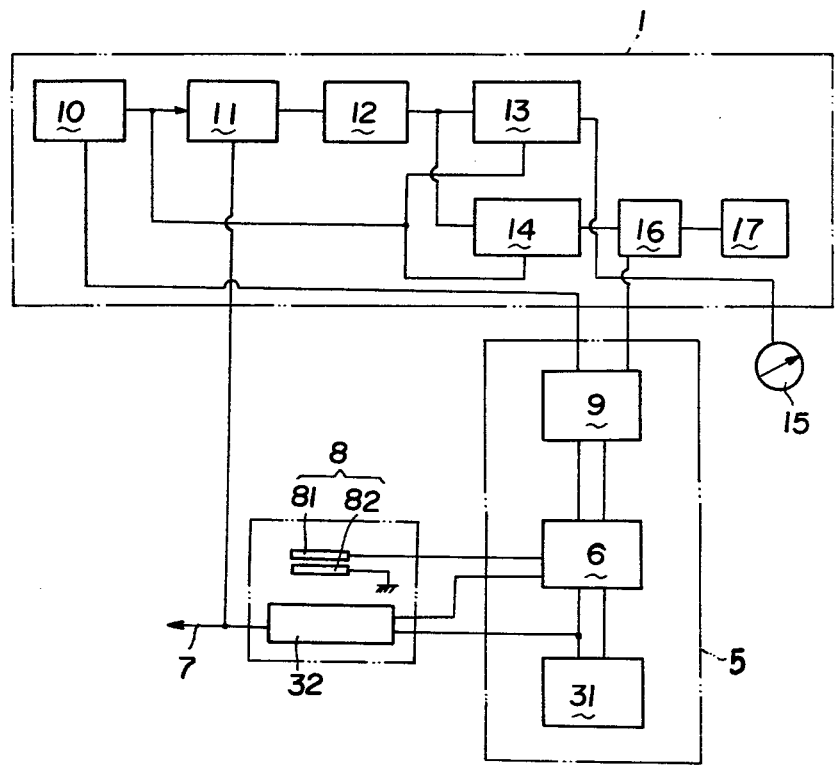
Figure 4:
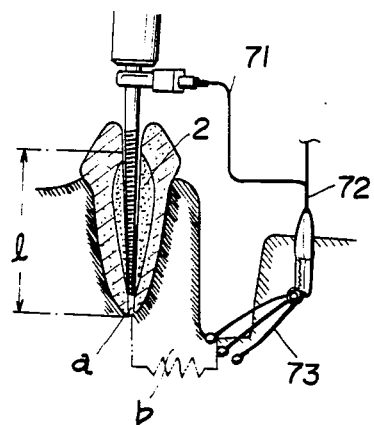
Figure 5:
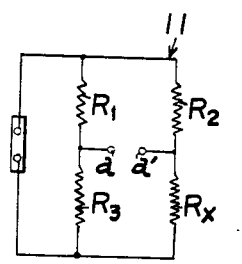

In the drawings;

FIG. 1 is a fragmentary side view of a dental engine, parts of which are shown in section, and a rear portion of which is omitted, FIG. 2 is a perspective view of the hand engine under operation and connected to a control device which is made in accordance with this invention, FIG. 3 is a wiring diagram of the hand engine and the control device, FIG. 4 is an explanatory view showing the working principle of this novel instrument, and FIG. 5 illustrates a bridge circuit employed in the control device.

Now, with reference to the drawings, numeral 1 shows in general a control device for measuring a depth of a root canal of a tooth, and by which the position of an apex a (FIG. 4) of the root is recognizable be reading a pointer provided on said device. As illustrated in in FIG. 4, when a reamer 7, which is supplied with very low or micro current, is driven into a dental pulp 2 within the canal, the pointer of the control device 1 indicates an infinitely great electric resistance, while when the reamer is drilled further into the canal, the electric resistance which is readable by the control device drops down to about 9 kΩ. And, when the forward end of the reamer 7 reaches a point adjacent to the radical apex a, the electric resistance becomes substantially constant, viz., about 7–6.5 KΩ. The electric resistance becomes finally 6.27 KΩ when the reamer reaches the apex a. This electric resistance of said 6.27 KΩ is common to man, because it is the electric resistance value that oral mucosae of human beings have. Hence, if the graduation of the control device 1 is made so as to indicate an electric resistance in the range of 9 KΩ to 6.27 KΩ, one can know, through the pointer, a position of a radical apex and consequently a depth l of a tooth root canal.

Numeral 10 (FIG. 3) indicates a conventional transmitting circuit which is operated by direct current supplied from an electric source 31, and which is connected to a bridge circuit 11 at the next stage. This bridge circuit 11 charges the dental reamer 7 with a micro current, and measures, when the reamer is drilled into the dental pulp 2, electric resistance of the canal by Wheatstone bridge method. To wit, when there is established an equation represented by $R_1 \times R_x = R_2 \times R_3$, a value of $R_x$ can be obtained from this equation if $R_1$–$R_3$ are known at the time when a voltage between a and a' is zero. This means also that since $R_x$ is obtainable by a voltage between a and a' (the electric resistance of a root canal), the value of said $R_x$ can be set as a zero point on the graduation 15. The resistance values which are then converted to current values, are indicated by the graduation.

Numeral 12 indicates an amplifier circuit which is to amplify weak signals sent from the bridge circuit 11 to its positive and negative poles, and is connected to phase discrimination circuits 13, 14. The phase discrimination circuits are connected in parallel so that they are operable respectively by signal at the positive and negative poles of the amplifier circuit. The phase discrimination circuit 14 operated at the negative pole controls 0–30uA, while the phase discrimination circuit 13 operated at the positive pole controls 30–40uA. This 30–40uA shows an area in which the forward end of reamer 7 is adjacent to the radical apex a. The electric resistance when the reamer is going to reach the apex is set as a standard of zero, and is shown as 30uA on the graduation. The graduation of 40uA then corresponds to the radical apex. When the reamer 7 is drilled into the dental pulp 2, the pointer first returns to a graduation of lesser values (in a direction of the arrow in FIG. 2), and returns back to a graduation of greater value from the graduation of 30uA when the reamer approaches the radical apex. In other words, the pointer 15 reciprocates to show a position of the reamer.

Numeral 16 is a camparison circuit for operating a warning circuit 17. When out-puts of the phase discrimination circuits 13, 14 in the preceding stage become larger than a predetermined voltage, it operates the warning circuit 17. In this embodiment, it works at 38uA Said warning circuit 17 of a stable multivibrator and a phase generator, not shown, and is charged with 38uA when the reamer 7 reaches a position near the radical apex, and gives thereby a warning signal or sound. It is contained in a casing 18.

Numeral 3 shows a cylindrical body of the dental hand engine A, which contains an engine 32 driven by a current from an electric source 31. More particularly, said engine 32 is connected at its positive pole to the aforementioned electric source 31 in case 5 by means of a connecting wire 4 which extends from the body 3 at the rear end thereof. The negative pole of said engine is connected to a touch switch circuit 6. When a current flows in said circuit, a driving shaft 33 rotates to transmit its rotation to a chuck 35 by means of a transmission shaft 34. Said chuck 35 has thereon an operating nut 36 for enabling reamers 7 of various diameters to be removably fastened in the chuck. It also has a head 37.

Numeral 8 indicates a touch switch, which is located at such position where a forefinger is brought naturally when the body 3 is held by fingers. It comprises a circular positive terminal 81 and circular negative terminals 82, 82, which are insertedly fitted within a circular recess 38 of the body 3. Said negative terminals are grounded, while the positive terminal is connected to the touch switch circuit 6. When a finger presses said terminals 81, 82, 82, the engine 32 starts to move.

Numeral 9 is a control circuit which can override the touch switch and turn circuit 6 off in preference to the touch switch. This control circuit is connected to the comparison circuit 16, and switches off the touch switch circuit 6 in accordance with signals from the comparison circuit 16. Numeral 91 indicates a variable resistance.

Numeral 71 indicates a terminal for sending a micro current to the reamer 7, which is connected to the bridge circuit 11. To the forward end of a ground wire 72, there is provided a clip 73 for connecting it to oral mucosae.

Numeral 83 is a ring which has a cut-out portion and which is rotatably fitted over the switch 8 for exposing said switch at a desired location or angle.

With the above described constructions, when the reamer 7 reaches a radical apex, it automatically stops on account of the aforementioned device 1. It certainly makes a dentist's operation of this kind easier, safe and accurate.

What is claimed is:

1. A dental hand engine for driving a reamer for widening a root canal of tooth, which comprises a body containing the engine and operable by fingers, switch means provided on said body for selectively operating the engine and the reamer connected to said engine, means for passing a micro current through the reamer, and electric circuit means for sensing electric resistances of the micro current passing through the reamer and for stopping the engine and reamer in response to a specific electric resistance said micro current has when the reamer reaches a radical apex.

* * * * *